United States Patent [19]

Naito et al.

[11] 4,172,829
[45] Oct. 30, 1979

[54] 2,9-DISUBSTITUTED ADENINE DERIVATIVES AND THEIR USE AS NON-ADRENERGIC BRONCHODILATORS

[75] Inventors: Takayuki Naito, Kawasaki; Susumu Nakagawa, Tokyo; Tetsuro Yamasaki; Taka-aki Okita, both of Ichikawa; Haruhiro Yamashita, Tokyo, all of Japan

[73] Assignee: Bristol-Myers Company, New York, N.Y.

[21] Appl. No.: 904,146

[22] Filed: May 9, 1978

[51] Int. Cl.² .......................................... C07D 473/02
[52] U.S. Cl. ................................... 424/253; 544/276; 544/277
[58] Field of Search .................. 544/277, 276; 424/253

[56] References Cited

U.S. PATENT DOCUMENTS

| 3,917,837 | 11/1975 | Lin et al. .............................. 424/253 |
| 3,930,005 | 12/1975 | Wojnar et al. ........................ 424/253 |

FOREIGN PATENT DOCUMENTS 2610985  9/1977  Fed. Rep. of Germany.

OTHER PUBLICATIONS

Farmdoc 70719y (Belgian Patent 853,086).
JACS 81, 197–201 (1959).
Farmdoc 53190y (Japanese Patent 52-71492).
Chem. Pharm. Bull. 23(4), 759–774 (1975).
Chem. Pharm. Bull. 25(7), 1811–1821 (1977).

*Primary Examiner*—Nicholas S. Rizzo
*Attorney, Agent, or Firm*—David M. Morse

[57] ABSTRACT

Purine derivatives of the formula

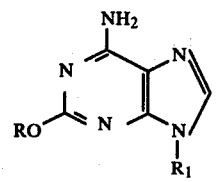

I wherein R is $C_1$–$C_6$ alkyl and $R_1$ is

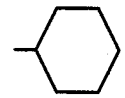

or

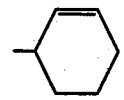

and their pharmaceutically acceptable acid addition salts are non-adrenergic bronchodilators.

24 Claims, No Drawings

2,9-DISUBSTITUTED ADENINE DERIVATIVES AND THEIR USE AS NON-ADRENERGIC BRONCHODILATORS

BACKGROUND OF THE INVENTION

1. Field of the Invention

This invention relates to novel purine derivatives useful as non-adrenergic bronchodilators.

2. Description of the Prior Art

Theophylline, normally administered as the ethylenediamine salt (aminophylline) or choline salt, is a potent and useful non-adrenergic bronchodilator commonly prescribed for the treatment of bronchial asthma. Because it is readily soluble, aminophylline has for many years been accepted as an effective bronchodilator when given orally. Aminophylline, however, is known to have certain disadvantages, e.g. gastric irritation and cardiovascular and central nervous system side effects, which warrant a search for new non-adrenergic bronchodilators which may have more advantageous properties such as increased potency and/or reduced side effects.

With respect to the novel compounds of the present invention, a vast number of purine derivatives have been disclosed in the patent and scientific literature. Illustrative of such references are the following:

1. *J. Am. Chem. Soc.*, 81, 197–201 (1959) discloses the synthesis of compounds having the formula

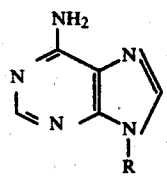

wherein R is cyclohexyl or 2-cyclohexenyl. The compounds were prepared as potential anticancer agents.

2. U.S. Pat. No. 3,917,837 discloses the use of the compound

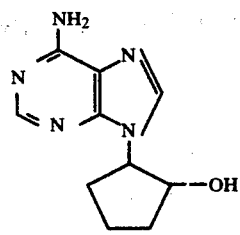

as an anti-inflammatory agent.

3. U.S. Pat. No. 3,930,005 discloses compounds of the formula

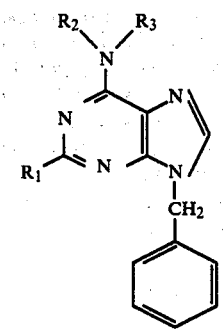

wherein $R_2$ and $R_3$ may be inter alia hydrogen and $R_1$ may be inter alia (lower)alkoxy. The compounds are said to possess anti-inflammatory activity.

4. Belgian Pat. No. 853,086 (Farmdoc 70719Y) discloses compounds of the formula

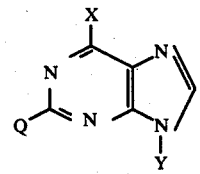

wherein either X is $C_1$–$C_6$ alkoxy or -NHR; R is H or (lower)alkyl; Y is $C_1$–$C_6$ alkyl, $C_3$–$C_{10}$ cycloalkyl or hydroxycycloalkyl, phenyl, halophenyl, trifluoromethyl-phenyl, bicycloalkyl or hydroxybicycloalkyl of up to 12 carbons, or -AR$^1$; A is methylene or ethylene; R$^1$ is phenyl, halophenyl, trifluoromethyl-phenyl, bicycloalkyl or hydroxybicycloalkyl of up to 12 carbons; Q is H, $C_1$–$C_6$ alkyl, $C_3$–$C_{10}$ cycloalkyl or hydroxycycloalkyl, bicycloalkyl or hydroxybicycloalkyl of up to 12 carbons, phenyl, halophenyl, trifluoromethyl-phenyl or AR$^1$; or X is halogen or (lower)dialkylamino; Y is methyl, ethyl, cyclopentyl, phenyl, halophenyl, trifluoromethyl-phenyl or benzyl and Q is as previously defined. The compounds are reported to be useful in treating psoriasis.

5. West German Published Application No. 2,610,985 (Farmdoc 70863Y) discloses compounds of the formula

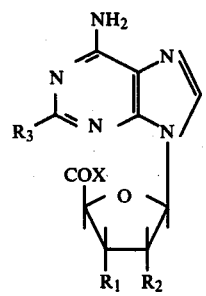

wherein $R_1$ and $R_2$ are OH or $ONO_2$, or together form $C_2$–$C_7$ alkylidene, aralkylidene or $CR_4R_5$; $R_4$ is H or $C_1$–$C_7$ alkyl; $R_5$ is $OR_6$ or $NR_7R_8$; $R_6$ is $C_1$–$C_7$ alkyl; $R_7$ and $R_8$ are optionally substituted $C_1$–$C_7$ alkyl or $C_3$–$C_7$ cycloalkyl, or together form a $C_2$–$C_5$ alkylene group in which one $CH_2$ group is optionally replaced by a heteroatom; $R_3$ is $C_1$-$C_7$ alkyl or alkoxy, optionally substituted phenyl or H; X is $OR_9$ or $NR_{10}R_{11}$; $R_9$ is $C_1$-$C_7$ alkyl, $C_3$-$C_7$ cycloalkyl, optionally substituted phenyl or aralkyl; $R_{10}$ and $R_{11}$ are H, optionally substituted $C_1$-$C_7$ alkyl, alkenyl or alkynyl, optionally substituted $C_3$-$C_7$ cycloalkyl, substituted phenyl, benzylamino, 2-methylfuryl or adamantyl, or one can be H and the other a group of the formula

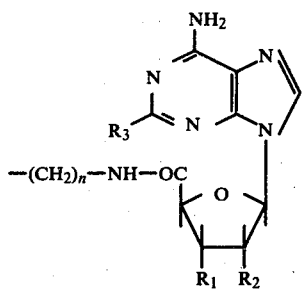

wherein n is 2-16, or $R_{10}$ and $R_{11}$ together form a $C_2$-$C_5$ alkylene group in which one $CH_2$ group can be replaced by a heteroatom. The compounds are said to have circulatory, cardiac and metabolic activity.

6. *Chem. Pharm. Bull.*, 23(4), 759-774 (1975) discloses inter alia compounds of the formula

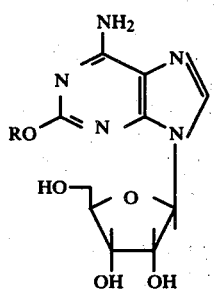

wherein R is (lower)alkyl. The compounds are said to have coronary vasodilating activity.

7. Japanese Published Application 52-71492 (Farmdoc 53190Y) discloses compounds of the formula

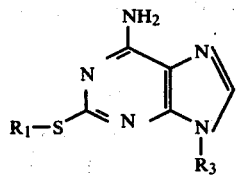

wherein $R_1$ is $C_1$-$C_{10}$ straight or branched alkyl, $C_5$-$C_{10}$ cycloalkyl, $C_7$-$C_{11}$ aralkyl or piperazinoethyl of the formula

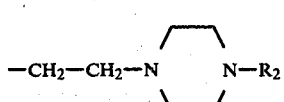

wherein $R_2$ is $C_7$-$C_{11}$ aralkyl, mono-substituted aralkyl, cinnamyl or fluorenyl; $R_3$ is $C_1$-$C_{10}$ straight or branched alkyl, $C_5$-$C_{10}$ cycloalkyl, $C_7$-$C_{11}$ aralkyl or piperazinoethyl as defined above, with the exclusion of compounds in which $R_1$ and $R_3$ are methyl, $R_1$ is methyl and $R_3$ is ethyl and $R_1$ is $C_5$-$C_{10}$ cycloalkyl and $R_3$ is $C_1$-$C_4$ alkyl, $C_5$-$C_{10}$ cycloalkyl or $C_7$-$C_{11}$ aralkyl. The compounds are reported to show an inhibitory effect on blood platelet aggregation and to have coronary dilating activity.

8. *Chem Pharm. Bull.*, 25(7), 1811-1821 (1977) discloses preparation of 2-thioadenosine derivatives including inter alia a compound of the formula

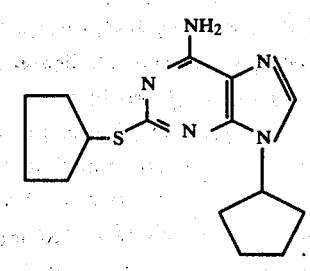

The above compound is reported to be slightly effective as a platelet aggregation inhibitor. The authors note that the corresponding compound having a ribose sugar moiety at the 9-position was far more effective and conclude that the ribosyl moiety of 2-thioadenosine derivatives is essential for effective inhibition of platelet aggregation and cannot be replaced by other substituents.

No references have been found disclosing 2,9-disubstituted adenine derivatives having an alkoxy substituent as the 2-position and a cycloalkyl or cycloalkenyl group at the 9-position.

SUMMARY OF THE INVENTION

The present invention is concerned with novel purine derivatives that effectively inhibit bronchial constriction induced by histamine or other bronchial constricting substances. The compounds belong to the non-adrenergic class of bronchodilators and are useful for administration to mammals in the treatment of asthma including bronchial asthma, allergic asthma, bronchitis, pulmonary emphysema and other chronic respiratory diseases involving bronchospasm. The preferred compounds of the invention have been shown by standard pharmacological test procedures to have superior bronchodilator activity relative to aminophylline with reduced cardiovascular and central nervous system side effects.

The compounds of the present invention have the structure

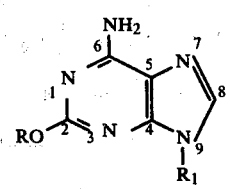

and pharmaceutically acceptable acid addition salts thereof, wherein R is $C_1$-$C_6$ alkyl and $R_1$ is

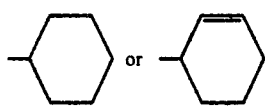

The term "pharmaceutically acceptable acid addition salts" as used herein includes those salts formed from mineral acids such as hydrochloric, hydrobromic, hydroiodic, nitric, sulfuric, phosphoric, and the like; and also organic acids such as acetic, citric, pivalic, lactic, tartaric, oxalic, succinic, maleic, and the like. Any nontoxic acid which forms a salt with the present compounds is suitable. The salts are prepared by conventional methods well-known to the art.

The $C_1$–$C_6$ alkyl groups referred to above include those having either straight or branched hydrocarbon chains. Particularly preferred alkyl groups are those having from 1 to 4 carbon atoms. Examples of suitable $C_1$–$C_6$ alkyl groups include methyl, ethyl, n-propyl, isopropyl, n-butyl, isobutyl, t-butyl, n-pentyl, n-hexyl, and the like.

The most preferred compounds included within formula I are those wherein R is $C_2H_5$-, n-$C_3H_7$- or n-$C_4H_9$-. Such compounds when subjected to standard in vitro and in vivo tests for bronchodilator activity exhibited superior potency relative to aminophylline. They also demonstrated reduced cardiovascular and central nervous system side effects when compared with the aminophylline reference agent.

The present invention also includes within its scope the novel intermediates of the formula

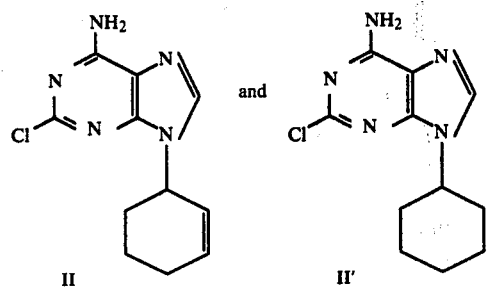

which can be readily converted by the processes described below into the compounds of formula I. Intermediates II and II' and pharmaceutically acceptable acid addition salts thereof also exhibit advantageous bronchodilator activity.

DETAILED DESCRIPTION OF THE INVENTION

The compounds of formula I may be prepared by the general reaction scheme depicted below.

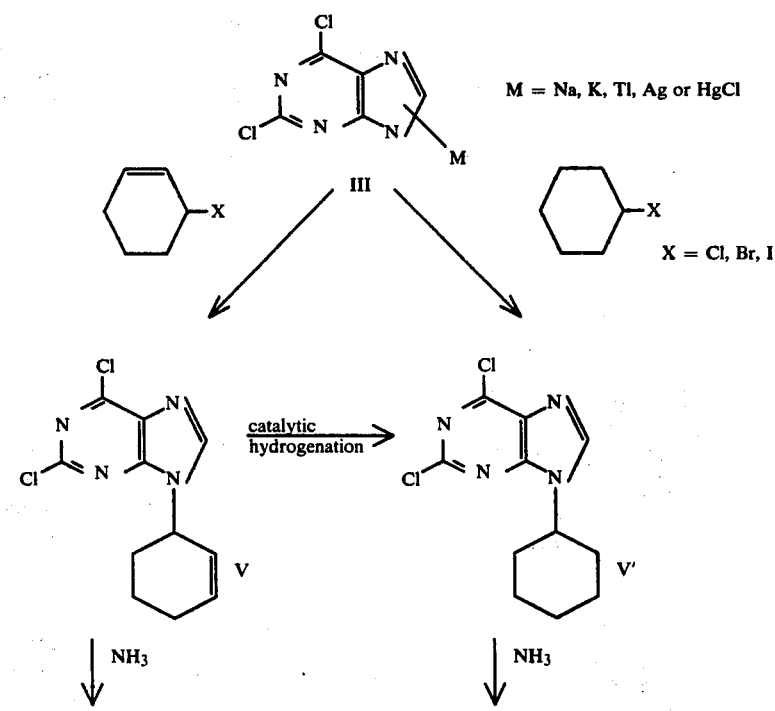

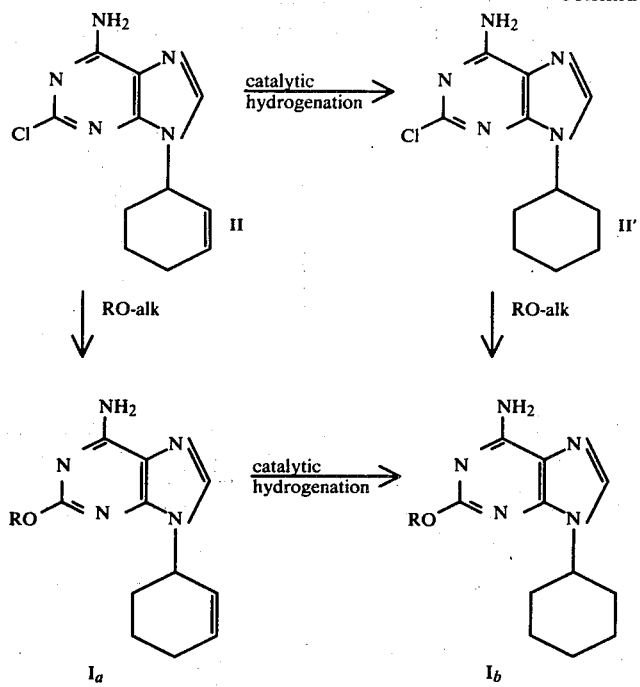

Compounds of formula I wherein $R_1$ is 2-cyclohexenyl may be prepared from 2,6-dichloropurine, a known compound, by the process comprising the consecutive steps of (1) reacting 2,6-dichloropurine with about one equivalent of $HgCl_2$ or a source of $Na^+$, $K^+$, $Tl^+$ or $Ag^+$ (i.e. a salt which dissociates to form the desired ion) in an inert solvent to produce a metal derivative having the formula

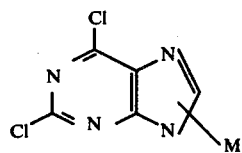

wherein M is HgCl, Na, K, Tl or Ag;

(2) condensing metal derivative III in a substantially anhydrous inert organic solvent with a 3-halocyclohexene of the formula

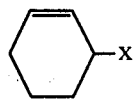

wherein X is chloro, bromo or iodo to produce an intermediate having the formula

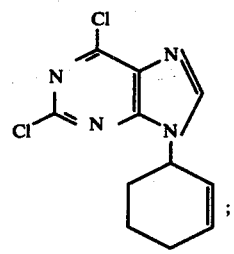

(3) subjecting intermediate V to amination with $NH_3$ in an inert solvent to produce an intermediate having the formula

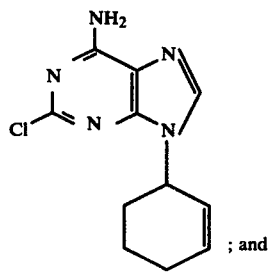

(4) heating intermediate II with an alkali metal alkoxide of the formula RO-alk wherein alk represents sodium or potassium and R is as defined above in an inert solvent to produce the desired free base product of formula I and, if desired, converting said product by methods known per se to a pharmaceutically acceptable acid addition salt thereof.

A preferred embodiment of the present invention comprises the step of preparing a compound of the formula

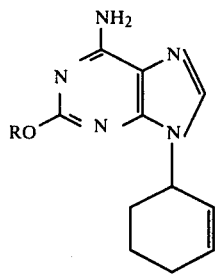

I_a wherein R is $C_1$–$C_6$ alkyl, or a pharmaceutically acceptable acid addition salt thereof, by heating intermediate II with an alkali metal alkoxide of the formula RO-alk wherein alk represents sodium or potassium and R is as defined above in an inert solvent until the desired free base product is formed and, if desired, converting said product by methods known per se to a pharmaceutically acceptable acid addition salt thereof.

Compounds of formula I wherein $R_1$ is cyclohexyl may be prepared by catalytic hydrogenation of the corresponding products having $R_1$=cyclohexenyl. As an example of a suitable procedure, a compound of formula $I_a$ may be dissolved in a suitable non-reducible, inert solvent (e.g. methanol, ethanol, water, aqueous methanol, aqueous ethanol) and then hydrogenated using a conventional hydrogenation catalyst. Examples of suitable catalysts include palladium black, Pd-BaSO$_4$, Pd-C, PtO$_2$, Ru-C, Rh-C, Raney nickel, CuCrO, RhCl[P(C$_6$H$_5$)$_3$]$_3$ and RuCl[P(C$_6$H$_5$)$_3$]$_3$. A preferred catalyst is palladium-on-carbon. While temperature and pressure are not critical for the hydrogenation step, advantageous results have been achieved under conditions of room temperature and atmospheric pressure.

An alternative process for preparing compounds of formula I wherein $R_1$ is cyclohexyl comprises the consecutive steps of (1) reacting 2,6-dichloropurine with about one equivalent of HgCl$_2$ or a source of Na$^+$, K$^+$, Tl$^+$, or Ag$^+$ in an inert solvent to produce metal derivative III;

(2) condensing metal derivative III in a substantially anhydrous inert organic solvent with a cyclohexyl halide of the formula

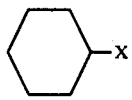

IV' wherein X is chloro, bromo or iodo to produce an intermediate having the formula

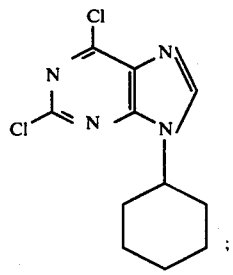

V'

(3) subjecting intermediate V' to amination with NH$_3$ in an inert solvent to produce an intermediate having the formula

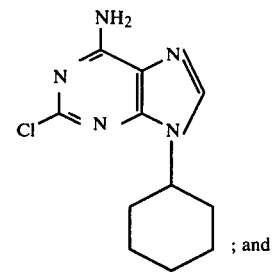

II'

; and (4) heating intermediate II' with an alkali metal alkoxide of the formula RO-alk wherein alk represents sodium or potassium and R is as defined above in an inert solvent to produce the desired free base product of formula I and, if desired, converting said product by methods known per se to a pharmaceutically acceptable acid addition salt thereof.

A preferred embodiment of the present invention comprises the step of preparing a compound of the formula

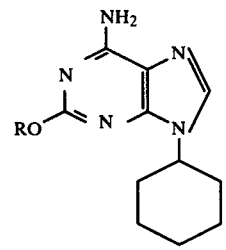

I_b wherein R is $C_1$–$C_6$ alkyl, or a pharmaceutically acceptable acid addition salt thereof, by heating intermediate II' with an alkali metal alkoxide of the formula RO-alk wherein alk represents sodium or potassium and R is as defined above in an inert solvent until the desired free base product is formed and, if desired, converting said product by methods known per se to a pharmaceutically acceptable acid addition salt thereof.

As can be seen from the general reaction scheme disclosed above, the present invention is intended to include within its scope all variants of the above described process for preparing compounds $I_b$ from 2,6-dichloropurine wherein either of intermediates V' or II' is prepared via ccatalytic hydrogenation of the corresponding cyclohexenyl intermediate. Thus, for example, the process might comprise preparing intermediate III, preparing intermediates V and II, catalytically hydrogenating II to II' and then preparing $I_b$ from II'. An alternative route would be III→V→V' (by catalytic hydrogenation)→II'→$I_b$. The reaction conditions previously described for catalytic hydrogenation of $I_a$→$I_b$ may be employed also in the conversions of V→V' or II→II'.

Preparation of the 2,6-dichloropurine metal derivatives of formula III may be accomplished by methods previously described in the literature.

The silver derivature of 2,6-dischloropurine may be prepared according to the general procedure disclosed in *J. Am. Chem. Soc.*, 73, 1650 (1951), i.e., the 2,6-dichloropurine is dissolved in boiling water, the solution is basified (e.g. with aqueous ammonia) and an aqueous solution of about one equivalent of a silver salt (e.g. AgNO₃) is added to form the desired 2,6-dichloropurine silver salt.

The sodium salt of 2,6-dichloropurine may be prepared according to the general procedure described in *Chem. Pharm. Bull.*, 25, 1811 (1977), i.e., the 2,6-dichloropurine is suspended in an inert solvent such as dimethylformamide and about one equivalent of a sodium salt such as NaOH or NaOCH₃ is added to form the desired salt in situ.

The potassium salt of 2,6-dichloropurine may be prepared according to the general procedures disclosed in *J. Am. Chem. Soc.*, 81, 197 (1959) and *J. Org. Chem.*, 81, 2310 (1963), i.e., 2,6-dichloropurine is dissolved in an inert solvent such as dimethylsulfoxide or dimethylformamide and an equimolar amount of a potassium salt such as K₂CO₃ is added to form in situ the desired metal salt.

The thallium (I) salt of 2,6-dichloropurine may be prepared according to the general procedure disclosed in *J. Org. Chem.*, 34, 1170 (1969), i.e. by addition of a thallium (I) salt such as thallium (I) ethoxide to a solution of 2,6-dichloropurine in an inert solvent such as ethanol.

The chloromercuri salt of 2,6-dischloropurine may be prepared by methods previously used with other purines, e.g. see *J. Org. Chem.*, 22, 954–959 (1957). The 2,6-dichloropurine is added to about one equivalent weight of HgCl₂ in an inert aqueous or aqueous organic solvent, e.g. an aqueous C₁–C₆ alkanol such as 50% ethanol. A base such as an aqueous solution of an alkali metal hydroxide (e.g. NaOH, KOH) is then added with stirring. Sufficient base is used to produce a permanent slight yellow color (due to HgO formation) which is indicative of the conclusion of the reaction step. The chloromercuri salt is the preferred metal derivative for use in the processes of the present invention.

Metal derivative III is condensed with a 3-halocyclohexene, preferably 3-bromocyclohexane, or a cyclohexyl halide to produce, respectively, intermediate V or V'. Reaction conditions may be substantially the same as those employed in the conventional nucleoside synthesis [see, e.g. *J. Am. Chem. Soc.*, 81, 197–201 (1959)]. In a preferred embodiment the 3-halocyclohexene or cyclohexyl halide is added, preferably in excess, to compound III in an inert substantially anhydrous organic solvent such as an aromatic hydrocarbon (e.g. benzene, xylene, toluene) and the reaction mixture is heated under reflux to form intermediate V or V'.

Amination of the so-produced intermediate to replace the 6-chloro substituent with a 6-amino group may be carried out by conventional procedures [see, e.g. *Chem. Pharm. Bull.*, 23, 759–774 (1975)]. In a preferred embodiment intermediate V or V' is suspended in an inert solvent (e.g. water, methanol, ethanol), the suspension is saturated with ammonia gas (preferably at a reduced temperature such as ~0° C.) and the saturated reaction mixture is then heated at a temperature of from just above room temperature to the boiling point of the reaction medium. A most preferred amination procedure comprises heating a solution of the appropriate intermediate in methanolic ammonia in a sealed tube at about 100° C. As noted above, compounds II and II' are potent bronchodilator agents as well as intermediates in the preparation of the 2-alkoxy products of formula I.

Intermediate II or II' may then be subjected to a nucleophilic substitution reaction to convert the 2-chloro substituent to a 2-alkoxy group. This step may be carried out by the general procedure disclosed in West German Published Application 2,258,378. In a preferred embodiment intermediate II or II' is heated with a solution of an alkali metal (lower)alkoxide (RONa or ROK where R is C₁–C₆ alkyl) in an inert solvent (e.g. benzene, dimethylformamide or a C₁–C₆ alkanol). If a (lower)alkanol solvent is used, both the alkanol and alkoxide used in this step should contain the same "R" substituent. While the temperature for the reaction is not critical, it is preferred to carry out the substitution at reflux temperature so as to maximize the yield and minimize the reaction time. At the conclusion of the reaction, any excess base in the reaction mixture is neutralized with acid and the desired free base product recovered as by evaporation to dryness.

Free base products of formula I, II or II' may be converted to pharmaceutically acceptable acid addition salts by conventional methods. Thus, for example, the free base may be dissolved in an inert solvent, reacted with about one equivalent weight of a suitable organic or inorganic acid to produce the desired salt, and the salt recovered as by solvent precipitation or lyophilization.

In another aspect the present invention provides a method for the reduction of bronchial constriction in a mammal afflicted with said condition which comprises administering to said mammal an effective bronchodilating amount of a compound of the formula

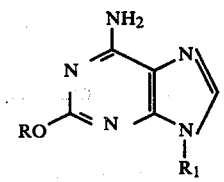

wherein R is C₁–C₆ alkyl and R₁ is

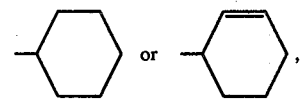

or or a pharmaceutically acceptable acid addition salt thereof. Most advantageously this method is carried out using the 2-alkoxy derivatives of formula I mentioned above as being particularly preferred.

In yet another aspect the present invention provides a pharmaceutical composition in dosage unit form which is useful for the relief of bronchial constriction in mammals. The composition comprises, as the active ingredient, an effective bronchodilating amount of a compound of formula I above, or a pharmaceutically acceptable acid addition salt thereof, in admixture with a pharmaceutically acceptable carrier or diluent. The preferred compositions are those in which the active ingredient is a compound of formula I mentioned above as being particularly preferred.

The pharmacologically active compounds of the present invention may be administered either as individual therapeutic agents or as mixtures with other therapeutic agents. They may be administered alone, but are generally given in the form of pharmaceutical compositions. Examples of such compositions include tablets, lozenges, capsules, powders, aerosol sprays, aqueous or oily suspensions, syrups, elixirs and aqueous solutions. The compounds are preferably administered orally, but may also be given by inhalation or injection.

The nature of the pharmaceutical composition and the pharmaceutical carrier or diluent will, of course, depend on the desired route of administration. For example, oral compositions may be in the form of tablets or capsules and may contain conventional excipients such as binding agents (e.g. syrup, acacia, gelatin, sorbitol, tragacanth or polyvinylpyrrolidone), fillers (e.g. lactose, sugar, maizestarch, calcium phosphate, sorbitol or glycine), lubricants (e.g. magnesium stearate, talc, polyethylene glycol or silica), disintegrants (e.g. starch) or wetting agents (e.g. sodium lauryl sulfate). Oral liquid preparations may be in the form of aqueous or oily suspensions, solutions, emulsions, syrups, elixirs, etc. or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of formula I with conventional pharmaceutical vehicles may be employed, e.g. as an aerosol spray for inhalation, as an aqueous solution for intravenous injection or as an oily suspension for intramuscular injection.

The compounds of formula I or pharmaceutical compositions thereof may be administered to mammals (including especially human patients) in oral dosages of from about 0.1 to 20 mg./kg./day of active ingredient. For intravenous administration to human patients, single doses of from about 0.02–5 mg./kg./dose of active ingredient may be used. Suitable human doses for aerosol administration are in the range of about 0.1–20 mg./dose of active ingredient. These values are illustrative only, however, and the physician of course will ultimately determine the dosage most suitable for a particular patient on the basis of such factors as age, weight, severity of the symptoms and the particular agent to be administered.

Pharmacological Tests

Representative compounds of the present invention were examined comparatively with aminophylline to determine in vitro and in vivo bronchodilator activity and in vivo hypotensive activity (a measure of cardiovascular side effect).

In Vitro Bronchodilator Activity

Tracheal chains of guinea pig were prepared by the method described by A. Akcasu in *Arch. Int. Pharmacodyn. Ther.*, 122, 201 (1959). The response to each test compound was recorded by the Magnus method and expressed as a percentage of the maximum response obtained with 0.1 mcg./ml. of isoproterenol prior to each experiment. Bronchodilator activity (in vitro) of aminophylline and the test compounds is expressed in Table 1 below as an $EC_{50}$ value (concentration in mcg./ml. which produces a relaxation which is 50% of the maximum response to 0.1 mcg./ml. of isoproterenol).

In Vivo Bronchodilator and Hypotensive Activity

The in vivo bronchodilator activity of aminophylline and the test compounds was evaluated by an increase in the intratracheal pressure (ITP) of guinea pig by a modification of the method described by James in *J. Pharm. Pharmac.*, 21, 379 (1969). The trachea of anesthetized guinea pig was cannulated and the ITP recorded on a polygraph under artificial ventilation. Arterial blood pressure (ABP; measure of hypotensive activity) was also measured during the experiment. Data was obtained for both intravenous and intraduodenal administration. Table 1 expresses the in vivo bronchodilator activity (ITP) of each compound as an $ED_{50}$ value (dose in mg./kg. resulting in a 50% decrease in intratracheal pressure) and the hypotensive activity (ABP) as an $ED_{20}$ value (dose in mg./kg. which reduces arterial blood pressure by 20%).

Separation of Bronchodilator and Cardiovascular Effects

To assess the separation of desirable bronchodilator activity from undesirable cardiovascular (hypotensive) effect in the test compounds, the ratio of hypotensive $ED_{20}$/bronchodilating $ED_{50}$ was calculated and indicated in Table 1. Those compounds exhibiting the largest ABP/ITP ratios have the greatest separation of cardiovascular side effect from bronchodilator activity.

Table 1

Pharmacological Test Results

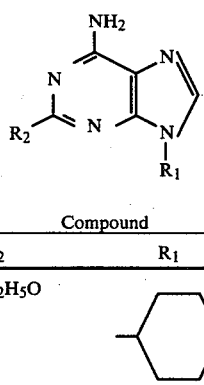

| | | In vitro | Intravenous In vivo | | | Intraduodenal | | |
|---|---|---|---|---|---|---|---|---|
| Compound | | ITC, $EC_{50}$ | ITP, $ED_{50}$ | ABP, $ED_{50}$ | | ITP, $ED_{50}$ | ABP, $ED_{50}$ | |
| $R_2$ | $R_1$ | (mcg./ml.) | (mg./kg.) | (mg./kg.) | ABP/ITP | (mg./kg.) | (mg./kg.) | ABP/ITP |
| $C_2H_5O$ | | 0.18 | 0.37 | 2.5 | 6.8 | | | |
| n-$C_3H_7O$ | " | 0.026 | 0.37 | 4.4 | 12 | 1.2 | 18 | 15 |
| n-$C_4H_9O$ | " | 0.025 | 0.0030 | 4.4 | 1467 | 1.4 | 8.3 | 5.9 |
| iso-$C_4H_9O$ | " | 0.31 | >3 | >3 | — | | | |
| n-$C_5H_{11}O$ | " | 1.8 | >3 | >3 | — | | | |
| n-$C_6H_{13}O$ | " | 1.4 | >3 | >3 | — | | | |

Table 1-continued
Pharmacological Test Results

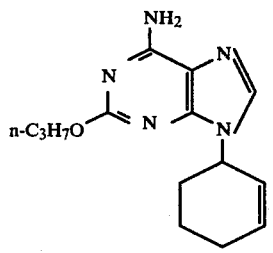

| Compound | | In vitro | In vivo | | | Intraduodenal | | |
|---|---|---|---|---|---|---|---|---|
| | | | Intravenous | | | | | |
| | | ITC, EC$_{50}$ | ITP, ED$_{50}$ | ABP, ED$_{50}$ | | ITP, ED$_{50}$ | ABP, ED$_{50}$ | |
| R$_2$ | R$_1$ | (mcg./ml.) | (mg./kg.) | (mg./kg.) | ABP/ITP | (mg./kg.) | (mg./kg.) | ABP/ITP |
| C$_2$H$_5$O | 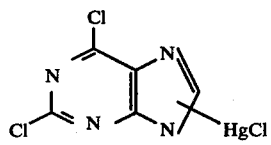 | 0.088 | 0.33 | 4.0 | 12 | 0.62 | 12 | 19 |
| n-C$_3$H$_7$O | " | 0.027 | 0.34 | 2.0 | 5.9 | 1.2 | 2.4 | 2.0 |
| n-C$_4$H$_9$O | " | 0.045 | 0.65 | >3 | >4.8 | | | |
| iso-C$_4$H$_9$O | " | 0.41 | >3 | 2.4 | — | | | |
| n-C$_5$H$_{11}$O | " | 0.59 | >3 | >3 | | | | |
| n-C$_6$H$_{13}$O | " | >3 | >3 | 2.7 | | | | |
| Cl | " | 0.12 | 0.15 | 2.5 | 17 | | | |
| aminophylline | " | 16.6 | 0.58 | 1.18 | 2 | 5.9 | 9.5 | 16 |

ITC = activity in the isolated tracheal chain
ABP = arterial blood pressure lowering activity
ITP = activity in the intratrachael pressure test The following examples are intended to be illustrative of the present invention.

EXAMPLE 1

9-(2-Cyclohexenyl)-2-n-propoxy-9H-adenine

A. HgCl Salt of 2,6-dichloropurine

To a stirred solution of 7.38 g. (27.2 mmoles) of HgCl$_2$ in 100 ml. of 50% ethanol was added 5.15 g. (27.2 mmoles) of 2,6-dichloropurine. After 5 minutes, 10% NaOH (~10 ml.) was added to the solution until no more color reaction (yellow due to HgO) occurred. The mixture was stirred for 30 minutes and the precipitate was filtered, washed successively with water, ethanol and diethyl ether, and dried to give 6.91 g. (64% yield) of the title salt.

B. 9-(2-Cyclohexenyl)-9H-2,6-dichloropurine

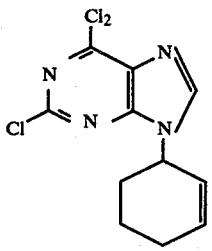

A mixture of 6.91 g. (16.3 mmoles) of the product of step A and 6.91 g. of "Celite" (diatomaceous earth) in benzene was azeotropically evaporated to remove moisture. To the resulting mixture was added 100 ml. of dry xylene and 4 ml. (339 mmoles) of 3-bromocyclohexene. The mixture was refluxed for 2.5 hours with agitation, cooled and filtered. The filter cake was washed with a small amount of CHCl$_3$. The filtrate and wash were evaporated to dryness. The residue was dissolved in 50 ml. of benzene and the solution washed with 20% KI solution (3 times) and aqueous NaCl (once) and dried with Na$_2$SO$_4$. The filtrate was evaporated and the residue purified by chromatography on silica gel to give 3.87 g. (88%) of the title intermediate; m.p. 133°–135° C. IR(KBr): 2930, 1590, 1565, 1405, 1355, 1315, 1210, 875, 835 cm$^{-1}$. UV: $\lambda_{max}^{MeOH}$ 276 nm ($\epsilon$ 9500). NMR(CDCl$_3$): δ 2.00(6H, m), 5.60(1H, m), 6.00(2H, m), 8.11(1H, s).

Anal. Calcd for C$_{11}$H$_{10}$N$_4$Cl$_2$: C, 49.09; H, 3.75; N, 20.82 Cl, 26.35. Found: C, 48.54; H, 3.48; N, 20.34; Cl, 25.54.

C. 2-Chloro-9-(2-cyclohexenyl)-9H-adenine

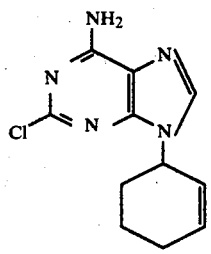

Ammonia gas was bubbled into a mixture of 2.8 g. (10.3 mmoles) of 9-(2-cyclohexenyl)-9H-2,6-dichloropurine in 50 ml. of CH₃OH at 0° C. until no more gas was absorbed. The mixture was heated at 100° C. for 4 hours in a sealed tube, then cooled and concentrated to deposit crystals, which were filtered to afford 2.39 g. of the title compound. A second crop (112 mg.) was obtained from the filtrate by chromatographical separation over silica gel. Total yield = 2.50 g. (96%); m.p. 195°–197° C. IR(KBr): 3120, 1640, 1590, 1320, 1300, 1225, 1190, 920 cm⁻¹. UV: $\lambda_{max}^{MeOH}$ 266 nm ($\epsilon$ 14600). NMR(CDCl₃): δ 0.89(1H, m), 1.26(1H, m), 2.00 (4H, m), 5.30(1H, m), 6.00(2H, m), 8.11(1H, s).

D. 9-(2-Cyclohexenyl)-2-n-propoxy-9H-adenine

A solution of 2.4 g. (9.2 mmoles) of 2-chloro-9-(2-cyclohexenyl)-9H-adenine in 60 ml. of 1 N sodium n-propoxide in n-propanol was heated at reflux overnight under a nitrogen atmosphere. The reaction mixture was poured into ice-water containing sufficient acetic acid to neutralize the excess alkoxide. The mixture was evaporated in vacuo. The residue was dissolved into CHCl₃ with stirring. The CHCl₃ extracts were washed with water, dried with Na₂SO₄ and evaporated to give 2.35 g. (90%) of title product; m.p. 157°–159° C. IR(KBr): 3450, 3110, 1630, 1585, 1470, 1390, 1335 cm⁻¹. UV: $\lambda_{max}^{MeOH}$ 266 nm ($\epsilon$ 13200). NMR(CDCl₃): δ 1.03 (3H, t, J=7 Hz), 1.80(8H, m), 4.15(2H, t, J=7 Hz), 5.03 (2H, m), 5.88(1H, m), 6.56(2H, m), 7.4(1H, s).

EXAMPLE 2

9-Cyclohexyl-2-n-propoxy-9H-adenine

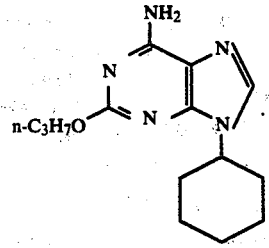

A solution of 2.21 g. (7.8 mmoles) of 9-(2-cyclohexenyl)-2-n-propoxy-9H-adenine in 30 ml. of 90% ethanol was hydrogenated overnight with 250 mg. of 10% Pd-C and then filtered. The filtrate was evaporated in vacuo, giving a residue which was crystallized from ethyl acetate-n-hexane. Yield 1.85 g. (76%); m.p. 148°–150° C. IR(KBr): 3510, 2930, 1670, 1640, 1595, 1405 cm⁻¹. UV: $\lambda_{max}^{MeOH}$ 252 nm ($\epsilon$ 8360), 269 nm ($\epsilon$ 13200). NMR(CDCl₃): δ 1.03(3H, t, J=7 Hz), 1.80(12H, m), 4.20(2H, t, J=7 Hz), 4.35(1H, m), 6.02(2H, s), 7.55(1H, s).

Anal. Calcd for C₁₄H₂₁N₅O: C, 61.07; H, 7.69; N, 25.43. Found: C, 61.07; H, 7.89; N, 25.48.

EXAMPLE 3

9-(2-Cyclohexenyl)-2-ethoxy-9H-adenine

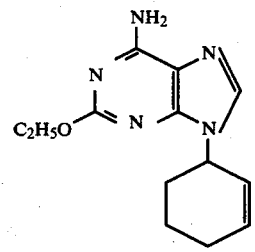

A mixture of 2-chloro-9-(2-cyclohexenyl)-9H-adenine (310 mg., 1.24 mmole) and a solution of sodium ethoxide in ethanol (0.25-1 N, ~10 ml.) was refluxed overnight under an atmosphere of nitrogen. The reaction mixture was poured into ice-water, neutralized with 1 N HCl and extracted with ethyl acetate (20 ml.). The extracts were washed with water, dried over Na₂SO₄ and filtered. The filtrate was evaporated and the residue then subjected to silica gel chromatography (silica gel 7 g., eluted with 1% CH₃OH-CHCl₃) to give the title product in 92% yield; m.p. 67°–72° C. IR(KBr): 3320, 2940, 1640, 1595, 1465, 1410, 1385, 1340 cm⁻¹. UV: $\lambda_{max}^{EtOH}$ 254 nm ($\epsilon$ 8400), 269 nm ($\epsilon$ 12600). NMR(CDCl₃): 1.44 (3H, t, J=7 Hz), 2.00(6H, m), 4.45(2H, q, J=7 Hz), 5.20(1H, m), 5.95(2H, m), 6.16(2H, s), 7.62(1H, s).

EXAMPLE 4

9-(2-Cyclohexenyl)-2-n-butoxy-9H-adenine

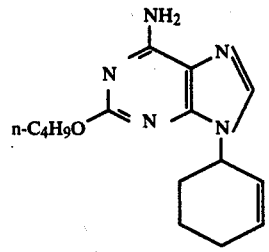

The procedure of Example 3 was repeated except that the sodium ethoxide in ethanol solution was replaced by an equivalent amount of sodium n-butoxide in n-butanol. There was produced the title product (as a hygroscopic powder) in 40% yield. IR(KBr): 3310, 3160, 2930, 1640, 1595, 1410, 1345 cm⁻¹. UV: $\lambda_{max}^{EtOH}$ 254 nm ($\epsilon$ 8300), 270 nm ($\epsilon$ 11500). NMR(CDCl₃): 1.80(13H, m), 4.23(2H, t, J=7 Hz), 5.02(1H, m), 5.84(2H, m), 6.06(2H, s), 7.58(1H, s).

EXAMPLE 5

9-(2-Cyclohexenyl)-2-n-pentyloxy-9H-adenine

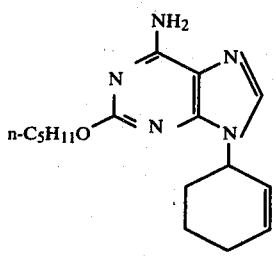

The procedure of Example 3 was repeated except that the sodium ethoxide in ethanol solution was replaced by an equivalent amount of sodium n-pentyloxide in n-pentanol. There was produced the title product (as a hygroscopic powder) in 48% yield. IR(neat): 3500, 3320, 2970, 1635, 1590, 1500, 1465, 1400, 1335 cm$^{-1}$. UV: $\lambda_{max}^{EtOH}$ 253 nm($\epsilon$ 8400), 269 nm ($\epsilon$ 12500). NMR(CDCl$_3$): 1.80(15H, m), 4.25(2H, t, J=6.5 Hz), 5.07(1H, m), 5.89(2H, m), 6.08(2H, s), 7.56(1H, s).

EXAMPLE 6

9-(2-Cyclohexenyl)-2-n-hexyloxy-9H-adenine

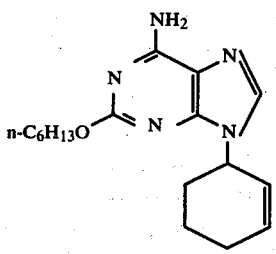

The procedure of Example 3 was repeated except that the sodium ethoxide in ethanol solution was replaced by an equivalent amount of sodium n-hexyloxide in n-hexanol. There was produced the title product (as a hygroscopic powder) in 26% yield. IR(neat): 3500, 3320, 1635, 1590, 1460, 1395, 1340 cm$^{-1}$. UV: $\lambda_{max}^{EtOH}$ 252 nm($\epsilon$ 6900), 268 nm($\epsilon$ 10200). NMR(CDCl$_3$): 1.50(17H, m), 4.25(2H, t, J=6 Hz), 5.08(1H, m), 5.86(2H, m), 6.01(2H, s), 7.60(1H, s).

EXAMPLE 7

9-(2-Cyclohexenyl)-2-isobutoxy-9H-adenine

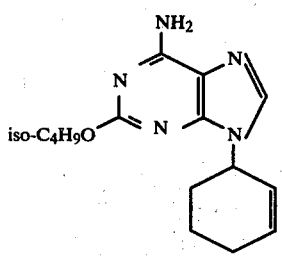

The procedure of Example 3 was repeated except that the sodium ethoxide in ethanol solution was replaced by an equivalent amount of sodium isobutoxide in isobutanol. There was produced the title product in 66% yield; m.p. 132°-135° C. IR(neat): 3025, 1630, 1590, 1460, 1395, 1375, 1350 cm$^{-1}$. UV: $\lambda_{max}^{EtOH}$ 253 nm($\epsilon$ 8600), 269 nm($\epsilon$ 13000). NMR(CDCl$_3$): 0.98(6H, d, J=6.5 Hz), 1.90(7H, m), 3.96(2H, d, J=6.5 Hz), 5.02(1H, m), 5.83(2H, m), 6.18(2H, s), 7.50 (1H, s).

EXAMPLE 8

2-Ethoxy-9-cyclohexyl-9H-adenine

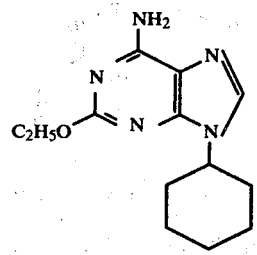

A mixture of 9-(2-cyclohexenyl)-2-ethoxy-9H-adenine (0.5 mmole) and 10% palladium-on-charcoal (35 mg.) in ethanol (6 ml.) was hydrogenated at room temperature and under atmospheric pressure. The reaction mixture was filtered and the filtrate was evaporated. The residue was lyophilized to give the title product in 40% yield; m.p. 134°-136° C. IR(KBr): 3280, 2995, 1705, 1615, 1525, 1415, 1310, 1010 cm$^{-1}$. UV: $\lambda_{max}^{EtOH}$ 253 nm($\epsilon$ 6800), 269 nm($\epsilon$ , 10200). NMR(CDCl$_3$): 1.44(3H, t, J=7 Hz), 2.00(10H, m), 4.45(2H, q, J=7 Hz), 4.50(1H, m), 8.07(1H, s), 8.60(2H, s).

EXAMPLE 9

2-n-Butoxy-9-cyclohexyl-9H-adenine

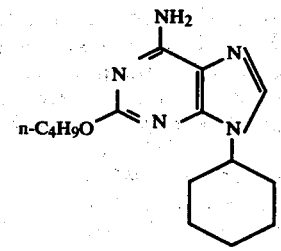

The procedure of Example 8 was repeated except that the 9-(2-cyclohexenyl)-2-ethoxy-9H-adenine used therein was replaced by an equivalent weight of 9-(2-cyclohexenyl)-2-n-butoxy-9H-adenine. There was produced the title product in 47% yield; m.p. 138°-141° C. IR(KBr): 3300, 2930, 1660, 1640, 1590, 1405, 1345 cm$^{-1}$. UV: $\lambda_{max}^{EtOH}$ 253 nm($\epsilon$ 7600), 269 nm($\epsilon$ 11500). NMR(CDCl$_3$): 1.50(17H, m), 4.30(1H, m), 4.31(2H, t, J=6 Hz), 6.40(2H, s), 7.67(1H, s).

EXAMPLE 10

2-n-Pentyloxy-9-cyclohexyl-9H-adenine

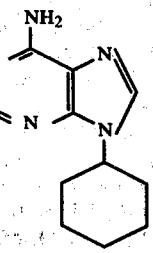

The procedure of Example 8 was repeated except that the 9-(2-cyclohexenyl)-2-ethoxy-9H-adenine used therein was replaced by an equivalent weight of 9-(2-cyclohexenyl)-2-n-pentyloxy-9H-adenine. There was produced the title product in 90% yield; m.p. 64°-68° C. IR(neat): 3500, 3320, 1635, 1590, 1460, 1395, 1340, 1325, 1265 cm$^{-1}$. UV: $\lambda_{max}^{EtOH}$ 253 nm($\epsilon$ 10900), 269 nm($\epsilon$ 16800). NMR(CDCl$_3$): 1.50(19H, m), 4.20(1H, m), 4.26(2H, t, J=6.5 Hz), 6.25(2H, s), 7.56(1H, s).

EXAMPLE 11

2-n-Hexyloxy-9-cyclohexyl-9H-adenine

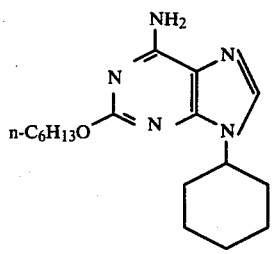

The procedure of Example 8 was repeated except that the 9-(2-cyclohexenyl)-2-ethoxy-9H-adenine used therein was replaced by an equivalent weight of 9-(2-cyclohexenyl)-2-n-hexyloxy-9H-adenine. There was produced the title product in 90% yield; m.p. 57°-60° C. IR(neat): 3500, 1635, 1595, 1500, 1465, 1420, 1400 cm$^{-1}$. UV: $\lambda_{max}^{EtOH}$ 253 nm($\epsilon$ 7200), 270 nm($\epsilon$ 10900). NMR(CDCl$_3$): 1.5(21H, m), 4.25(2H, t, J=6.5 Hz), 4.40(1H, m), 6.07(2H, s), 7.54(1H, s).

EXAMPLE 12

2-Isobutoxy-9-cyclohexyl-9H-adenine

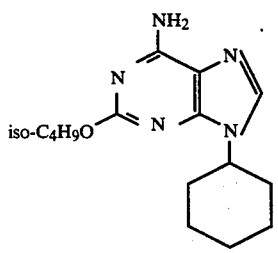

The procedure of Example 8 was repeated except that the 9-(2-cyclohexenyl)-2-ethoxy-9H-adenine used therein was replaced by an equivalent weight of 9-(2-cyclohexenyl)-2-isobutoxy-9H-adenine. There was produced the title product in 60% yield; m.p. 123°-134° C. IR(neat): 3320, 3160, 2940, 1635, 1590, 1395, 1375 cm$^{-1}$. UV: $\lambda_{max}^{EtOH}$ 253 nm($\epsilon$ 7000), 269 nm($\epsilon$ 11000). NMR(CDCl$_3$): 1.05(6H, d, J=6.5 Hz), 1.90(11H, m), 4.05(2H, d, J=6.5 Hz), 4.24(1H, m), 6.14(2H, s), 7.55(1H, s).

EXAMPLE 13

9-(2-Cyclohexenyl)-2-methoxy-9H-adenine

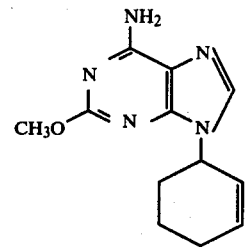

If the procedure of Example 3 is repeated with the sodium ethoxide in ethanol replaced by an equivalent amount of sodium methoxide in methanol, there is produced the title product.

EXAMPLE 14

2-Methoxy-9-cyclohexyl-9H-adenine

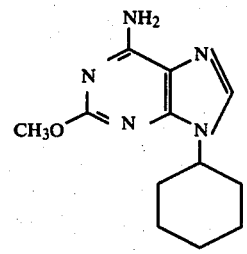

If the procedure of Example 8 is repeated with the 9-(2-cyclohexenyl)-2-ethoxy-9H-adenine used therein replaced by an equivalent weight of 9-(2-cyclohexenyl)-2-methoxy-9H-adenine, there is produced the title product.

EXAMPLE 15

2-n-Butoxy-9-cyclohexyl-9H-adenine (alternative process)

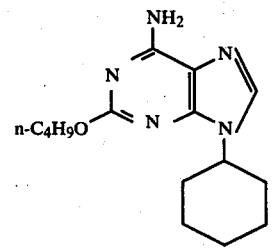

A. 9-Cyclohexyl-9H-2,6-dichloropurine

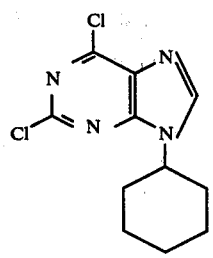

If in the procedure of Example 1B the 3-bromocyclohexene used therein is replaced by an equivalent weight of cyclohexyl bromide, the title intermediate is produced.

B. 2-Chloro-9-cyclohexyl-9H-adenine

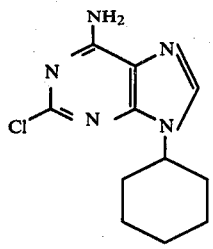

If the procedure of Example 1C is repeated with the 9-(2-cyclohexenyl)-9H-2,6-dichloropurine used therein replaced by an equivalent weight of 9-cyclohexyl-9H-2,6-dichloropurine, there is produced the title intermediate.

C. 2-n-Butoxy-9-cyclohexyl-9H-adenine

If the procedure of Example 4 is repeated with the 2-chloro-9-(2-cyclohexenyl)-9H-adenine used therein replaced by an equivalent weight of 2-chloro-9-cyclohexyl-9H-adenine, there is produced the title product.

EXAMPLE 16

2-n-Butoxy-9-cyclohexyl-9H-adenine (alternative process)

A. 2-Chloro-9-cyclohexyl-9H-adenine

A mixture of 2-chloro-9-(2-cyclohexenyl)-9H-adenine[1] (252 mg.; 1.0 mmol) in ethanol was hydrogenated with 10% palladium-on-charcoal (93 mg.) at room temperature and under atmospheric pressure. The reaction mixture was filtered and the filtrate was evaporated. The residue was purified by silica gel chromatography to give 139 mg. (55%) of the title compound; m.p. 206°–209° C. IR (KBr): 3360, 3150, 2905, 1645, 1595, 1570, 1540 cm$^{-1}$. UV: $\lambda_{max}^{C_2H_5OH}$ 267 nm($\epsilon$ 15,300). NMR (CDCl$_3$): δ 1.80 (10H, m), 4.47 (1H, m), 6.23 (2H, s), 7.82 (1H, s).

[1]. Prepared from 2,6-dichloropurine according to the procedure of Example 1.

B. 2-n-Butoxy-9-cyclohexyl-9H-adenine

If the procedure of Example 4 is repeated with the 2-chloro-9-(2-cyclohexenyl)-9H-adenine used therein replaced by an equivalent weight of 2-chloro-9-cyclohexyl-9H-adenine, there is produced the title product.

EXAMPLE 17

Hydrochloride Salt of 2-n-Butoxy-9-cyclohexyl-9H-adenine

Addition of a stoichiometric equivalent of HCl to a methanolic solution of 2-n-butoxy-9-cyclohexyl-9H-adenine gives the title salt.

We claim:
1. A compound of the formula

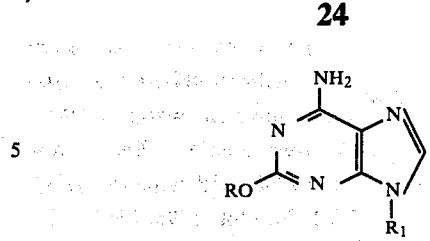

wherein R is $C_1$–$C_6$ alkyl and $R_1$ is

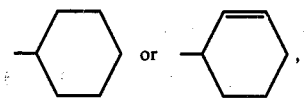

or a pharmaceutically acceptable acid addition salt thereof.

2. A compound of claim 1 wherein R is $C_2H_5$-, n-$C_3H_7$- or n-$C_4H_9$-.

3. A compound of the formula

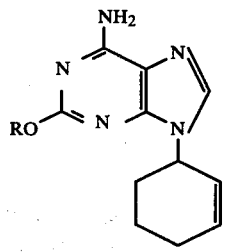

wherein R is $C_1$–$C_6$ alkyl, or a pharmaceutically acceptable acid addition salt thereof.

4. A compound of claim 3 wherein R is -$C_2H_5$-, n-$C_3H_7$- or n-$C_4H_9$-.
5. A compound of claim 3 wherein R is $CH_3$-.
6. A compound of claim 3 wherein R is $C_2H_5$-.
7. A compound of claim 3 wherein R is n-$C_3H_7$.
8. A compound of claim 3 wherein R is n-$C_4H_9$-.
9. A compound of claim 3 wherein R is iso-$C_4H_9$-.
10. A compound of claim 3 wherein R is n-$C_5H_{11}$-.
11. A compound of claim 3 wherein R is n-$C_6H_{13}$-.
12. A compound of the formula

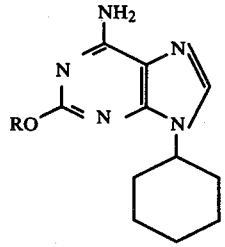

wherein R is $C_1$–$C_6$ alkyl, or a pharmaceutically acceptable acid addition salt thereof.

13. A compound of claim 12 wherein R is $C_2H_5$-, n-$C_3H_7$- or n-$C_4H_9$-.
14. A compound of claim 12 wherein R is $CH_3$-.
15. A compound of claim 12 wherein R is $C_2H_5$-.
16. A compound of claim 12 wherein R is n-$C_3H_7$-.
17. A compound of claim 12 wherein R is n-$C_4H_9$-.
18. A compound of claim 12 wherein R is iso-$C_4H_9$-.
19. A compound of claim 12 wherein R is n-$C_5H_{11}$-.
20. A compound of claim 12 wherein R is n-$C_6H_{13}$-.

21. A method for the reduction of bronchial constriction in a mammal afflicted with said condition which comprises administering to said mammal an effective bronchodilating amount of a compound of the formula

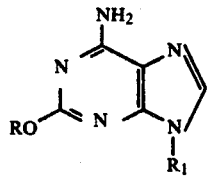

wherein R is $C_1-C_6$ alkyl and $R_1$ is

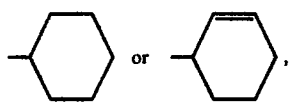

or a pharmaceutically acceptable acid addition salt thereof.

22. The method of claim 21 wherein the compound administered has the formula

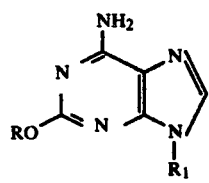

wherein R is $C_2H_5-$, $n-C_3H_7-$ or $n-C_4H_9-$ and $R_1$ is

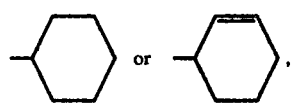

or a pharmaceutically acceptable acid addition salt thereof.

23. A pharmaceutical composition useful for the treatment of bronchial constriction which comprises a pharmaceutically acceptable carrier or diluent and an effective bronchodilating amount of a compound of the formula

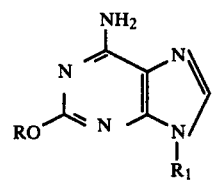

wherein R is $C_1-C_6$ alkyl and $R_1$ is

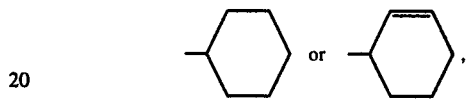

or a pharmaceutically acceptable acid addition salt thereof.

24. A composition according to claim 23 wherein the active ingredient is a compound of the formula

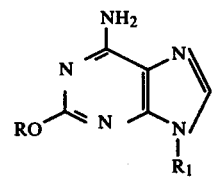

wherein R is $C_2H_5-$, $n-C_3H_7-$ or $n-C_4H_9-$ and $R_1$ is

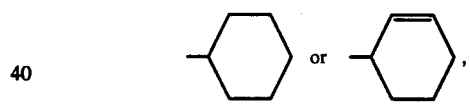

or a pharmaceutically acceptable acid addition salt thereof.

* * * * *